(12) United States Patent
Lou et al.

(10) Patent No.: US 11,324,679 B2
(45) Date of Patent: May 10, 2022

(54) METHOD FOR STABILIZING RETINOIC ACID PRECURSORS AND A SKIN BENEFIT COMPOSITION WITH STABILIZED RETINOIC ACID PRECURSORS

(71) Applicant: Conopco, Inc., Englewood Cliffs, NJ (US)

(72) Inventors: Anjing Lou, Seymour, CT (US); Teanoosh Moaddel, Watertown, CT (US); Anil Babubhai Patel, Parsippany, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 12 days.

(21) Appl. No.: 16/099,450

(22) PCT Filed: May 8, 2017

(86) PCT No.: PCT/EP2017/060962
§ 371 (c)(1),
(2) Date: Nov. 7, 2018

(87) PCT Pub. No.: WO2017/194486
PCT Pub. Date: Nov. 16, 2017

(65) Prior Publication Data
US 2020/0163849 A1 May 28, 2020

(30) Foreign Application Priority Data

May 12, 2016 (EP) ..................................... 16169468

(51) Int. Cl.
*A61K 8/34* (2006.01)
*A61K 8/06* (2006.01)
*A61K 8/36* (2006.01)
*A61Q 19/00* (2006.01)
*A61K 8/67* (2006.01)
*A61Q 19/08* (2006.01)
*A61K 8/35* (2006.01)

(52) U.S. Cl.
CPC .............. *A61K 8/347* (2013.01); *A61K 8/062* (2013.01); *A61K 8/361* (2013.01); *A61Q 19/00* (2013.01)

(58) Field of Classification Search
CPC .... A61K 2800/52; A61K 8/062; A61K 8/347; A61K 8/355; A61K 8/361; A61K 8/671; A61Q 19/00; A61Q 19/08
See application file for complete search history.

(56) References Cited

U.S. PATENT DOCUMENTS

| | | | |
|---|---|---|---|
| 4,826,828 A | 2/1989 | Wilmott et al. | |
| 5,887,747 A | 3/1999 | Burklin et al. | |
| 6,858,217 B2 | 2/2005 | Kerschner | |
| 6,869,598 B2 | 3/2005 | Love et al. | |
| 6,863,897 B2 | 8/2005 | Love et al. | |
| 7,250,158 B1 | 7/2007 | Shore et al. | |
| 8,299,127 B2 | 10/2012 | Anjing et al. | |
| 8,425,882 B2 | 4/2013 | Lou et al. | |
| 9,580,600 B2 | 2/2017 | Tamura et al. | |
| 9,839,588 B2 | 12/2017 | Matsuo et al. | |
| 2002/0143059 A1 | 10/2002 | Pillai | |
| 2003/0232091 A1 | 12/2003 | Shefer | |
| 2008/0311058 A1 | 12/2008 | Lou et al. | |
| 2009/0263513 A1 | 10/2009 | Marini | |
| 2010/0143445 A1 | 6/2010 | Pelisson et al. | |
| 2010/0316581 A1 | 12/2010 | Takeoka et al. | |
| 2012/0087872 A1 | 4/2012 | Tamarkin | |
| 2012/0101156 A1* | 4/2012 | Oddos .................... A61K 8/671 514/520 |
| 2013/0074860 A1 | 3/2013 | Colvan et al. | |
| 2013/0115177 A1 | 5/2013 | Stock et al. | |

FOREIGN PATENT DOCUMENTS

| | | |
|---|---|---|
| CN | 1642523 | 7/2005 |
| CN | 1482899 | 9/2008 |
| CN | 101415396 | 4/2009 |
| CN | 102451467 | 5/2012 |
| EP | 0093770 | 6/1991 |
| EP | 0815040 | 10/1996 |
| EP | 1269978 | 1/2003 |
| EP | 2572701 | 3/2013 |
| EP | 2921160 | 9/2015 |
| JP | 2004526690 | 9/2004 |
| JP | 2005526093 | 9/2005 |
| JP | 2010526124 | 7/2010 |
| JP | 2011001270 | 1/2011 |
| JP | 2014505687 | 3/2014 |
| WO | WO9630279 | 10/1996 |
| WO | WO02053124 | 7/2002 |
| WO | WO03080011 | 10/2002 |
| WO | WO03080011 | 10/2003 |

(Continued)

OTHER PUBLICATIONS

Google NPL search for isotretinoin anisatil; PubChem pdf attachmentl; downloaded May 19, 2020.*
Azelac RU by Sesderma, "Facial serum that delivers brighter, more luminous skin while helping to control hyperpigmentation for a more even skin tone."; Apr. 10, 2016; pp. 1-2.
Search Report and Written Opinion in EP16169468; dated Oct. 14, 2016.
IPRP2 in PCTEP2017060962; Jun. 25, 2018.
Effective Eye Serum ; Mintel GNPD Database ; 2013; pp. 1-4; XP002770955, Record ID: 2233097.

(Continued)

*Primary Examiner* — Jeffrey T. Palenik
(74) *Attorney, Agent, or Firm* — Stephanie S. DelPonte

(57) ABSTRACT

A method for stabilizing retinoic acid precursors and a skin benefit composition with stabilized retinoic acid precursors are described. The composition has a retinoic acid precursor and a resorcinol to impede oxidation of the precursor in situ in the composition.

17 Claims, No Drawings

(56) References Cited

FOREIGN PATENT DOCUMENTS

| WO | WO03105806 | 12/2003 | | |
|---|---|---|---|---|
| WO | WO2009072629 | 6/2009 | | |
| WO | WO2010113930 | 10/2010 | | |
| WO | WO2011049247 | 4/2011 | | |
| WO | WO2012094638 | 7/2012 | | |
| WO | WO2013044111 | 3/2013 | | |
| WO | WO 2014/139963 A1 * | 9/2014 | ............ | A61Q 17/04 |

OTHER PUBLICATIONS

Spotvest Anti-Brown Spot Radiance ; Mintel GNPD Database ; 2015; pp. 1-4; XP002770956, Record ID: 3512211.
Search Report and Written Opinion in PCTEP2017060962; dated Jul. 10, 2017.
Written Opinion in PCTEP2017060962; dated Mar. 26, 2018.
Gao Qinfeng; Biochemistry;.; Jun. 2006; pp. 86, (original & English abstractonly)total of 4 pages; .; China.
Sun Jingqi; Organic Chemistry;.; Jul. 2007;p49 (total of 4 pages, Original and English abstract translation);.
Qiu Bingyi, ; Modern cosmetics science and technique;.;Mar. 2016;p. 1807 (original and English abstract, total of 5 pages); vol. 2.
Qiu Bingyi; Modern cosmetics science and technique;.;Mar. 2016;p. 750 (original and English abstract only, tota of 4 pages); vol. 1.
Fan Zhongzhou; The latest therapy for beauty and ENT diseases;.; p. 9 (original and English abstract, total of 4 pages); China Population PublishingHouse; China, Dated Mar. 1995.
Ma Zhenyou; Skin beauty cosmetics formulation handbook;.; Mar. 2004;p. 220 (original and English abstract, total of 4 pages); Chinese; China.
Yu Maozhang; Newly com piledworld fine chemicals handbook;. ;Apr. 2000;p. 81 (original and English translation, total of 4 pages); Information Center of National Medical products administration; China.
Katsui, et al.; Research on Antioxidants (V): Vitamin A Antioxidant Power of Resorcinol Derivatives The Vitamin Society of Japan; 1952; pp. 342-345 (with Original and English Abstract only, 5 pages total).

* cited by examiner

METHOD FOR STABILIZING RETINOIC ACID PRECURSORS AND A SKIN BENEFIT COMPOSITION WITH STABILIZED RETINOIC ACID PRECURSORS

FIELD OF THE INVENTION

The present invention is directed to a method for stabilizing retinoic acid precursors and a skin benefit composition comprising such stabilized precursors. More particularly, the invention is directed to a method and skin benefit composition that use a skin benefit agent comprising a resorcinol and/or derivative thereof to prevent in situ oxidation of retinoic acid precursors. The compositions of this invention are surprisingly stable, free of malodour and discoloration, and do not irritate skin upon topical application.

BACKGROUND OF THE INVENTION

Many consumers find it desirable to deliver skin benefits via methods that rely on the application of topical compositions. This is especially true when consumers wish to look younger by reducing facial lines and wrinkles as well as blotchy color marks on the skin.

Minimizing cutaneous aging, both intrinsic and from photoaging, is often attempted with compositions with retinoic acid precursors. While such compositions can provide benefits to skin, instability of such precursors, typically the result of in situ oxidation, results in premature formation of retinoic acid as well as other oxidised compounds in packaged compositions and prior to application. This results in a product that may irritate a consumer's skin shortly after application, possesses a malodour and/or is tainted with discoloration. It could even result in a non-stable composition with oxidised compounds that do not necessarily have a positive impact on skin.

It is of increasing interest to develop a stable skin benefit composition that is suitable to provide benefits to skin and has reduced amounts of premature retinoic acid precursor oxidation.

This invention, therefore, is directed to a composition with stabilized retinoic acid precursors that have been stabilized with a skin benefit agent comprising a resorcinol. The composition of the present invention surprisingly can be topically applied without causing skin irritation, free of malodour and discoloration while simultaneously delivering excellent skin benefits. The inventive composition allows for better penetration of retinoic acid precursors into skin so that the same may convert to retinoic acid after penetration and for enhanced efficacy.

ADDITIONAL INFORMATION

Efforts have been disclosed for making formulations to treat skin. In U.S. Pat. No. 4,826,828, retinol comprising compositions with volatile silicones are described.

Still other efforts have been disclosed for making formulations to treat skin. In U.S. Pat. No. 8,299,127, a method and composition for evenly applying water soluble actives to skin is described.

Even other efforts have been disclosed for making formulations to treat skin. In EP0093770B1, compositions with retinoids and minoxidil for enhancing scalp hair growth are described.

U.S. Pat. Nos. 6,863,897, 6,869,598, and 6,858,217 all describe topical compositions with resorcinols.

None of the additional information above describes a composition with stabilized retinoic acid precursors that have been stabilized with a skin benefit agent comprising resorcinol.

SUMMARY OF THE INVENTION

In a first aspect, the present invention is directed to a composition comprising:
(a) a retinoic acid precursor;
(b) a skin benefit agent comprising resorcinol and/or a derivative thereof; and
(c) a cosmetically acceptable carrier
wherein the skin benefit agent impedes oxidation of the retinoic acid precursor and the retinoic acid precursor and the skin benefit agent comprising resorcinol and/or a derivative thereof are present at a weight ratio from 0.2 to 4 to 4 to 0.2, including all weight ratios subsumed therein.

In a second aspect, the present invention is directed to a method of impeding in situ oxidation of a retinoic acid precursor.

All other aspects of the present invention will readily become apparent upon considering the detailed description and examples which follow.

Skin, as used herein, is meant to include skin on the feet, face, neck, chest, back, arms, hands, legs, buttocks and scalp (including hair). The composition of this invention includes creams, lotions, balms, serums, deodorants and antiperspirants, shampoos, conditioners, bars and liquid wash products. In a preferred embodiment, the composition of this invention is a leave-on composition like a leave-on cream or lotion.

Skin benefit agent comprising resorcinol and/or a derivative thereof ("SBA") means an agent that is at least 25 percent by weight resorcinol and/or derivative thereof, and preferably 40 to 95 percent resorcinol and/or derivative thereof, and most preferably, all resorcinol and/or its derivatives. Skin benefit agent includes an agent that may be formulated in the composition of this invention to improve a skin characteristic. Retinoic acid precursor ("RAP") means a component that, when oxidized, can convert to retinoic acid. Examples of such a component include retinol, retinal, retinyl propionate, retinyl palmitate, hydroxyanasatil retinoate (i.e., Retextra®) mixtures thereof or the like. More preferred retinoic acid precursors in the context of the invention are retinal, retinyl propionate, retinyl palmitate, hydroxyanasatil retinoate (i.e., Retextra®) and mixtures thereof. Even more preferred are retinyl propionate, hydroxyanasatil retinoate (i.e., Retextra®) and mixtures thereof. Most preferred is hydroxyanasatil retinoate (i.e., Retextra®). Unless explicitly stated otherwise, all ranges described herein are meant to include all ranges subsumed therein. The term comprises is meant to encompass the terms consisting essentially of and consisting of. For the avoidance of doubt, a composition comprising retinoic acid precursor, resorcinol and a cosmetic carrier is also meant to include a composition consisting essentially of and a composition consisting of the same. All percentages used herein are meant to be by weight unless stated otherwise. The composition of this invention is meant to include a skin benefit composition suitable for sale and application (e.g., topically) by a consumer. The composition of the invention which is suitable to provide benefit to skin can be an emulsion or a composition that is free of water and emulsifier. Free of malodour and discoloration means surprisingly not any worse than control deplete of SBA. Stable, as used herein, means a measurable decrease in retinoic acid precursor oxidation within the composition (i.e., in situ). Resorcinol derivative means at least one H on the ring structure and/or on a hydroxy group of the resorcinol replaced with an alkyl group. The preferred resorcinol derivatives used in this invention are 4-substituted resorcinols.

Except in the operating and comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE INVENTION

The only limitation with respect to the retinoic acid precursors that may be used in the compositions of this invention is that the same are suitable for formulating into a composition that may be applied to human skin. Illustrative examples of the retinoic acid precursors that may be used in this invention include those represented by the formula

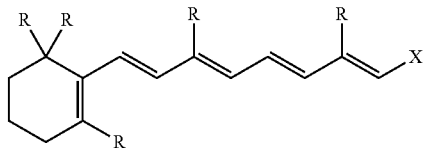

where each R is independently a hydrogen or a $C_{1-6}$ alkyl group and X is

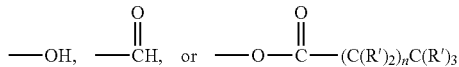

and further where each R' is hydrogen or a $C_1$-$C_3$ alkyl and n is an integer from 0 to 16 (preferably from 6 to 16, more preferably from 1 to 5).

Preferably the retinoic acid precursor comprises, more preferably is, retinol, retinal, retinyl propionate, retinyl palmitate or a mixture thereof. Even more preferably, the retinoic precursor comprises, more preferably is, retinyl proprionate, retinyl palmitate or a mixture thereof.

Still another retinoic acid precursor suitable for use is hydroxanasatil retinoate made commercially available under the name Retextra® as supplied by Molecular Design International. The same may be used in a mixture with the precursors described herein.

Typically the amount of retinoic acid precursor used in the compositions of this invention is from 0.001 to 10%, and preferably, from 0.01 to 6%, and most preferably, from 0.05 to 3.5%, based on total weight of the composition and including all ranges subsumed therein.

Regarding the skin benefit agent comprising resorcinol and/or derivative that may be used, the same is limited only to the extent that it is suitable for formulating in compositions, especially topical compositions.

Illustrative examples of the types of SBAs that may be used in this invention include those represented by the formula

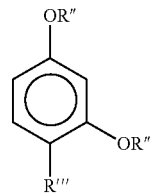

wherein each R" is independently hydrogen, or $C_{1-6}$ alkyl and R''' is hydrogen or a $C_{1-18}$ linear or branched alkyl.

Often, R" is hydrogen and the SBA is a resorcinol derivative like 4-methyl resorcinol, 4-ethyl resorcinol, 4-propyl resorcinol, 4-butyl resorcinol, 4-pentyl resorcinol, 4-hexyl resorcinol, 4-heptyl resorcinol, 4-octyl resorcinol, 4-isopropyl resorcinol, mixtures thereof or the like. It is preferred that the SBA in the context of the invention is 4-methyl resorcinol, 4-ethyl resorcinol, 4-propyl resorcinol, 4-butyl resorcinol, 4-pentyl resorcinol, 4-hexyl resorcinol, 4-heptyl resorcinol, 4-octyl resorcinol, 4-isopropyl resorcinol, mixtures thereof or the like. More preferably, the SBA is 4-methyl resorcinol, 4-ethyl resorcinol, 4-propyl resorcinol, 4-butyl resorcinol, 4-pentyl resorcinol, 4-heptyl resorcinol, 4-octyl resorcinol, 4-isopropyl resorcinol, mixtures thereof or the like. Even more preferably, the SBA is 4-ethyl resorcinol, 4-butyl resorcinol, 4-hexyl resorcinol, 4-isopropyl resorcinol, mixtures thereof or the like. A preferred SBA is 4-ethyl resorcinol. This preferred SBA or SBAs are preferably combined with the retinoic acid precursors preferred in the context of the invention that are retinal, retinyl propionate, retinyl palmitate, hydroxyanasatil retinoate (i.e., Retextra®) and mixtures thereof. Even more preferred are retinyl propionate, hydroxyanasatil retinoate (i.e., Retextra®) and mixtures thereof. More preferred are retinyl propionate, retinyl palmitate and mixtures thereof. Also hydroxyanasatil retinoate (i.e., Retextra®) can be a preferred RAP.

Typically, the amount of SBA used is from about 0.001 to 10%, and preferably, from 0.01 to 6%, and most preferably, from 0.1 to 3.5%, based on total weight of the composition and including all ranges subsumed therein.

The weight ratio of RAP to SBA is from 0.2:4 to 4:0.2, and preferably, from 0.2:3 to 3:0.2, and most preferably, from 0.25:1 to 1:0.25, including all ratios subsumed therein.

The compositions of this invention can have as cosmetically acceptable carriers non-polar liquids like oils comprising the RAP and SBA present at ratios as described herein. Alternatively, such non-polar liquids comprising the RAP and SBA can be used as the oil phase when the composition is an emulsion. The weight ratio of RAP to SBA can also be from 0.5:4.0 to 4.0:0.5.

When the compositions of the present invention are emulsions, they will typically include cosmetically acceptable carrier components in addition to non-polar liquid with RAP and SBA as described herein. In an often preferred embodiment the RAP and SBA are added as a pre-mix with a non-polar liquid to prepare the composition of this invention. Water is the most preferred additional carrier. Amounts of water may range from 1 to 99%, and preferably, from 5 to 90%, and most preferably, from 35 to 80%, and optimally, from 40 to 75% by weight, based on total weight of the composition and including all ranges subsumed therein.

Ordinarily the compositions of this invention will be water and oil emulsions, most preferably, of the oil-in-water variety. Water-in-oil emulsions, and especially, those generally classified as water-in-oil and high internal phase emulsions are, however, an option. Illustrative examples of the high internal phase emulsions suitable to carry the SBA and RAP of this invention are described in commonly owned U.S. Patent Application Publication No. 2008/0311058 and U.S. Pat. No. 8,425,882, the disclosures of which are incorporated herein by reference.

Other cosmetically acceptable carriers suitable for use (with or without water and also for use to combine RAP and SBA) in this invention may include mineral oils, silicone oils, esters, and alcohols. Amounts of these materials may collectively range from 0.1 to 99%, and preferably, from 0.1 to 45%, and most preferably, from 1 to 20% by weight of the composition of this invention, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms.

Linear volatile silicone materials generally have viscosities of less than 5 centistokes at 25° C. while cyclic materials typically have viscosities of less than about 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from 5 to 100,000 centistokes at 25° C.

An often preferred silicone source is a cyclopentasiloxane and dimethiconol solution.

Among suitable esters are:

(1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate;

(2) Ether-esters such as fatty acid esters of ethoxylated fatty alcohols;

(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 mono stearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;

(4) Wax esters such as beeswax, spermaceti, myristyl myristate, stearyl stearate; and (5) Sterol esters, of which soya sterol and cholesterol fatty acid esters are examples thereof.

Often, oils such as caprylic capric triglyceride are preferred as carriers.

Emulsifiers may be present in the compositions of the present invention. Total concentration of the emulsifier may range from about 0.1 to 40%, and preferably, from 1 to 20%, and most preferably, from 1 to 5% by weight of the composition, including all ranges subsumed therein. The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkyl ether carboxylates and combinations thereof.

Cationic emulsifiers that may be used include, for example, almitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, 1,2-octanediol, ethylhexylglycerine, hexylene glycol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition, including all ranges subsumed therein. Combinations of 1,2-octanediol and phenoxyethanol, or iodopropynyl butyl carbamate and phenoxyethaol are preferred, with phenoxyethanol making up from 35 to 65% by weight of the total weight of the preservative combination with the phenoxyethanol.

Thickening agents may optionally be included in compositions of the present invention. Particularly useful are the polysaccharides. Examples include starches, natural/synthetic gums and cellulosic s. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel 305 and taurate copolymers such as Simulgel EG and Arlstoflex AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from 0.001 to 5%, and preferably, from 0.1 to 2%, and most preferably, from 0.2 to 0.5% by weight of the composition and including all ranges subsumed therein.

Fragrances, fixatives and abrasives may optionally be included in compositions of the present invention. Each of these substances may range from about 0.05 to about 5%, preferably between 0.1 and 3% by weight.

To enhance skin moisturization, cationic ammonium compounds may optionally be used in the compositions of this invention to enhance moisturization. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri ($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from 0.01 to 30%, and preferably, from 0.1 to 15% by weight of the composition.

When cationic ammonium compounds are used, additional preferred additives for use with the same are moisturizing agents such as substituted ureas like hydroxymethyl urea, hydroxyethyl urea, hydroxypropyl urea; bis(hydroxymethyl) urea; bis(hydroxyethyl)urea; bis(hydroxypropyl)urea; N,N'-dihydroxymethyl urea; N,N'-di-hydroxyethyl urea; N,N'-dihydroxypropyl urea; N,N,N'-tri-hydroxyethyl urea; tetra (hydroxymethyl)urea; tetra(hydroxyethyl)urea; tetra(hydroxypropyl)urea; N-methyl-N'-hydroxyethyl urea; N-ethyl-N,N-N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the composition of this invention range from 0.01 to 20%, and preferably, from 0.5 to 15%, and most preferably, from 2 to 10% based on total weight of the composition and including all ranges subsumed therein.

Conventional humectants may be employed in the present invention as skin benefit agent and in addition to resorcinol and/or a derivative thereof. These are generally polyhydric alcohol type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 20%, preferably between 1 and 15% by weight of the composition.

When cationic ammonium compound and substituted urea are used, in a most especially preferred embodiment at least from 1 to 15% glycerin is used, based on total weight of the composition and including all ranges subsumed therein.

Compositions of the present invention may optionally include, along with resorcinol and/or derivative thereof, vitamins in addition to retinol (Vitamin A) present as a retinoic acid precursor. Illustrative vitamins are Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed and Vitamin D and K are also options. Total amount of optional vitamins when present in compositions according to the present invention may range from 0.0 to 10%, preferably from 0.001 to 1%, optimally from 0.01 to 0.5% by weight of the composition.

Other optional additives suitable for use in this invention include alpha-and/or beta-hydroxyacids, 12-hydroxystearic acid, petroselinic acid, conjugated linoleic acid, creatine, creatinine, retinoid boosters (e.g., climbazole, bibonazole, farnesole, glycyrrchetinic acid, ursolic acid, geranyl geraniol, oleyl betaine, hexanoyl sphingosine) mixtures thereof or the like. Such additives, when used, collectively make up from about 0.001 to about 12% by weight of the composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from 0.01 to 15% by weight of the composition of this invention.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary.

Also optionally suitable for use include materials like chelators (e.g., EDTA), opacifiers (like $TIO_2$, particle size from 50 to 1200 nm, and preferably, 50 to 350 nm), $C_8$-$C_{22}$ fatty acid substituted saccharides, lipoic acid, retinoxytrimethylsilane (available from Clariant Corp. under the SilCare IM-75 trademark), dehydroepiandrosterone (DHEA) and combinations thereof. Ceramides (including Ceramide I, Ceramide 3, Ceramide 36 and Ceramide 6) as well as pseudoceramides may also be useful. Amounts of these materials may range from 0.000001 to 10%, preferably from 0.0001 to 1% by weight of the composition of this invention.

Sunscreen actives may also be included in compositions of the present invention. Particularly preferred are such materials as ethylhexyl p-methoxycinnamate, available as Parsol MCX, Avobenzene, available as Parsol 1789 and benzophenone-3, also known as Oxybenzone. Inorganic sunscreen actives may be employed such as microfine titanium dioxide, octcrylene zinc oxide, polyethylene and various other polymers.

Amounts of the sunscreen agents when present may generally range from 0.1 to 30%, preferably from 0.5 to 20%, optimally from 0.75 to 10% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from 4 to 8, and preferably, from 4.25 to 7.75, and most preferably, from 6 to 7.5, including all ranges subsumed therein.

As previously noted, the SBA of the present invention can comprise in addition to resorcinol and/or derivatives thereof, additional skin benefit agents. It is preferred that resorcinol and/or derivatives thereof make up at least 25% by weight, and preferably, at least 40 to 95% by weight, and most preferably, 100% by weight of the SBA.

Any oil soluble optional skin benefit agents or additives may, if desired, be provided collectively with the SBA to make up the portion of the skin benefit agent that is not resorcinol and/or a derivative thereof. Without being bound by theory, it is believed that the SBA stabilizes retinoic acid precursor by impeding the oxidation of the same in situ (i.e., in composition).

The composition of the present invention preferably is a leave-on skin lotion, cream, shampoo, conditioner, shower gel, antiperspirant, deodorant, depilatory, shave cream or toilet bar.

The invention of the present invention further relates to a method for impeding oxidation of a RAP comprising the steps of combining, in no particular order, the RAP and SBA in a carrier they are soluble in and recovering a composition where oxidation of RAPs is impeded.

A wide variety of packaging can be employed to store and deliver the composition with stable retinoic acid precursors of this invention. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, nonaerosol pumps and flip-top hinged lids. Packaging for antiperspirants, deodorants and depilatories may involve a container with a roll-on ball on a dispensing end.

Alternatively these types of personal care products may be delivered in a stick composition formulation in a container with propel repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

The following examples are provided to facilitate an understanding of the present invention. The examples are not intended to limit the scope of the claims.

EXAMPLES

Example 1

Compositions were prepared with caprylic capric triglyceride as the carrier to 100%. Storage was maintained at 45° C. Assessment of RAP amount in the formulae was achieved via HPLC using ASTM Standards.

| | Initial RAP Concentration (%) and Percent RAP Remaining (weeks) | | | | | |
|---|---|---|---|---|---|---|
| RAP | Week 0 | Week 1 | Week 4 | Week 4 % Remaining | Week 20 | Week 20 % Remaining |
| Retextra®[1] | 0.36 | 0.14 | 0 | 0 | 0 | 0 |
| Retinyl Propionate | 0.38 | No Change | 0.32 | 84 | 0 | 0 |
| Retinol | 0.1 | 0.042 | 0.001 | 1 | 0 | 0 |
| Retextra & ER[2] | 0.33 | No change | 0.24 | 73 | 0.05 | 15 |
| Retinyl Propionate & ER | 0.4 | 0.39 | 0.35 | 88 | 0.222 | 56 |
| Retinol & ER | 0.1 | 0.087 | 0.01 | 10 | 0 | 0 |

[1] = made available by Molecular Design International, hydroxyanasatil retinoate

[2] = ER denotes 4-ethyl resorcinol, 0.35% in the composition which yellowed significantly slower (about 20% of the control based on visual inspection) when assessed after being stored for 4 weeks at 45 degrees celcius.

The results show that 4-ethyl resorcinol improves the stability of the RAPs by preventing oxidation.

Example 2

The experiments in Example 2 were conducted in a manner that was similar to the one described in Example 1 except 4-hexyl resorcinol (HR) was used as well. Resorcinol added at 0.35%. Caprylic capric triglyceride was the carrier added to balance, 100%.

| | Week 0 Concentration | Week 1 Concentration | Week 4 Concentration | Percent Remaining Week 0 | Week 1 | Week 4 |
|---|---|---|---|---|---|---|
| Retextra® & ER | 0.36 | 0.14 | 0 | 100 | 100 | 73 |
| Retextra® & HR | 0.34 | 0.34 | 0.29 | 100 | 100 | 85 |
| Retinyl Propionate & ER | 0.38 | 0.38 | 0.32 | 100 | 100 | 88 |
| Retinyl Propionate & HR | 0.37 | 0.37 | 0.37 | 100 | 100 | 100 |
| Retinol & ER | 0.1 | 0.087 | 0.01 | 100 | 87 | 10 |
| Retinol & HR | 0.1 | 0.093 | 0.04 | 100 | 93 | 40 |

The data provided demonstrates that the presence of resorcinol unexpectedly prevents the breakdown, oxidation of the RAP.

Example 3

The data provided in the experiments below demonstrate that when the SBA is present at a weight ratio of about 50% of the RAP, maximum stability is achieved.

| RAP/SBA | Ratio (weight %) | Week 0 Concentration | Week 1 Concentration | Week 4 Concentration |
|---|---|---|---|---|
| Retinyl Propionate/ER | 1:2 | 0.21 | 0.21 | 0.21 |
| Retinyl Propionate/ER | 1:1 | 0.4 | 0.39 | 0.35 |
| Retinyl Propionate/ER | 2:1 | 0.44 | 0.42 | 0.42 |
| Retinyl Propionate | — | 0.38 | 0.38 | 0.32 |
| Retinol/ER | 1:3 | 0.1 | 0.09 | 0.01 |
| Retinol/ER | 1:1 | 0.2 | 0.16 | 0.07 |
| Retinol/ER | 2:1 | 0.2 | 0.16 | 0.07 |
| Retinol | — | 0.1 | 0.042 | 0.001 |

The invention claimed is:

1. A composition comprising:
(a) a retinoic acid precursor, meaning a component that, when oxidized, can convert to retinoic acid, wherein the retinoic acid precursor is selected from retinyl propionate, hydroxyanasatil retinoate, and mixtures thereof;
(b) a skin benefit agent comprising resorcinol and/or a derivative thereof, wherein the derivative has at least one H on the ring structure and/or on a hydroxy group of the resorcinol replaced with an alkyl group, wherein the skin benefit agent comprising resorcinol and/or derivative thereof is selected from 4-ethyl resorcinol, 4-butyl resorcinol, 4-hexyl resorcinol, 4-isopropyl resorcinol and mixtures thereof; and
(c) a cosmetically acceptable carrier wherein the retinoic acid precursor and the skin benefit agent comprising resorcinol and/or a derivative thereof are present at a weight ratio of from about 1:2 to about 2:1.

2. The composition according to claim 1 wherein the retinoic add precursor is present from 0.001 to 10% by weight of the composition, and the skin benefit agent comprising resorcinol and/or a derivative thereof is present from 0,001 to 10% of the composition.

3. The composition according to claim 1 wherein the retinoic add precursor and skin benefit agent comprising resorcinol and/or derivative thereof are present in a weight ratio of about 1:1 to about 2:1.

4. The composition according to claim 1 wherein the retinoic acid precursor is hydroxyanasatil retinoate.

5. The composition according to claim 1, wherein the composition further comprises a retinoid booster selected from climbazole, bibonazole, farnesol, glycyrrhetinic acid, ursolic acid, geranyl geraniol, oleyl betaine, hexanoyl sphingosine, and mixtures thereof.

6. The composition according to claim 1 wherein the composition is not an emulsion.

7. The composition according to claim 1 wherein the composition is an oil-in-water emulsion.

8. The composition according to claim 1, wherein the composition further comprises a component selected from creatine, 1,2-octanediol, sunscreen, conjugated linoleic acid, hydroxyl acid, niacinamide, 12-hydroxystearic acid, phenoxyethanol, and mixtures thereof.

9. The composition according to claim 1 wherein the skin benefit agent comprising resorcinol and/or derivative thereof impedes oxidation of the retinoic acid precursor in the composition.

10. The composition according to claim 1 comprising:
(a) hydroxyanasatil retinoate;
(b) resorcinol derivative selected from 4-methyl resorcinol, 4-ethyl resorcinol, 4-butyl resorcinol, 4-pentyl resorcinol, 4-hexyl resorcinol, 4-heptyl resorcinol, 4-octyl resorcinol, 4-isopropyl resorcinol and mixtures thereof; and
(c) a cosmetically acceptable carrier; wherein said composition is a cosmetic composition;
wherein said hydroxyanasatil retinoate and said resorcinol derivative are present at a weight ratio of from about 1:2 to about 2:1 whereby said hydroxyanasatil retinoate is stabilized by said resorcinol derivative.

11. The composition according to claim 10 comprising hydroxyanasatil retinoate and a resorcinol derivative selected from 4-ethyl resorcinol and 4-hexyl resorcinol in a weight ratio of about 1:1.

12. The composition according to claim 1 wherein the skin benefit agent is 4-ethyl resorcinol or 4-hexyl resorcinol.

13. The composition according to claim 12 wherein the skin benefit agent is 4-ethyl resorcinol.

14. The composition according to claim 1 further comprising at least one component selected from glyceryl stearate, glycol stearate, stearamide AMP, PEG-100 stearate, and/or cetyl alcohol.

15. A method for impeding oxidation of a retinoic acid precursor in a composition comprising the step of combining the retinoic acid precursor with a skin benefit agent comprising resorcinol and/or derivative thereof wherein the retinoic acid precursor is selected from retinyl propionate, hydroxyanasatil retinoate, and mixtures thereof and the skin benefit agent is selected from 4-ethyl resorcinol, 4-butyl resorcinol, 4-hexyl resorcinol, 4-isopropyl resorcinol and mixtures thereof,
wherein the retinoic acid precursor and the skin benefit agent comprising resorcinol and/or a derivative thereof are present at a weight ratio of from about 1:2 to about 2:1.

16. A composition with a skin benefit agent comprising resorcinol and/or derivative thereof, the skin benefit agent impeding oxidation of a retinoic acid precursor in the composition, said retinoic acid precursor selected from retinyl propionate, hydroxyanasatil retinoate, and mixtures thereof, wherein the skin benefit agent is selected from 4-ethyl resorcinol, 4-butyl resorcinol, 4-hexyl resorcinol, 4-isopropyl resorcinol and mixtures thereof
wherein the retinoic acid precursor and the skin benefit agent comprising resorcinol and/or a derivative thereof are present at a weight ratio of from about 1:2 to about 2:1.

17. The composition according to claim 16, wherein the composition further comprises at least one component selected from creatine, 1,2-octanediol, sunscreen, conjugated linoleic acid, hydroxyl acid, niacinamide, 12-hydroxystearic acid, phenoxyethanol, glyceryl stearate, glycol stearate, stearamide AMP, PEG-100 stearate, cetyl alcohol, and/or a retinoid booster selected from climbazole, bibonazole, farnesol, glycyrrhetinic acid, ursolic acid, geranyl geraniol, oleyl betaine, hexanoyl sphingosine, and mixtures thereof.

* * * * *